United States Patent
Cavazza

(10) Patent No.: US 6,814,972 B2
(45) Date of Patent: Nov. 9, 2004

(54) COMPOSITION FOR PREVENTION AND/OR TREATMENT OF VASCULAR DISEASES, COMPRISING PROPIONYL L-CARNITINE AND COENZYME $Q_{10}$

(75) Inventor: Claudio Cavazza, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/220,186
(22) PCT Filed: Feb. 20, 2001
(86) PCT No.: PCT/IT01/00081
§ 371 (c)(1),
(2), (4) Date: Oct. 22, 2002
(87) PCT Pub. No.: WO01/64203
PCT Pub. Date: Sep. 7, 2001

(65) Prior Publication Data
US 2003/0059418 A1 Mar. 27, 2003

(30) Foreign Application Priority Data
Mar. 2, 2000 (IT) .................... RM2000A0106

(51) Int. Cl.$^7$ ............... A61K 6/00; A61K 7/00
(52) U.S. Cl. ............ 424/400; 424/439; 424/451; 424/464
(58) Field of Search ............... 424/400, 439, 424/94.1, 451, 464

(56) References Cited

U.S. PATENT DOCUMENTS 6,232,346 B1 * 5/2001 Sole et al. .................. 514/561

FOREIGN PATENT DOCUMENTS

| WO | WO 98/41113 | 9/1998 |
|----|-------------|--------|
| WO | WO 98/43617 | 10/1998 |
| WO | WO 00/00183 | 1/2000 |
| WO | WO 00/62773 | 10/2000 |
| WO | WO 00/64426 | 11/2000 |
| WO | WO 01/74361 | 10/2001 |

* cited by examiner

Primary Examiner—Thurman K. Page
Assistant Examiner—Konata M. George
(74) Attorney, Agent, or Firm—Nixon & Vanderhye P.C.

(57) ABSTRACT

A composition is disclosed which is suitable for the prevention and/or treatment of vasculopathic, cardiac, central and peripheral cerebral disturbances and for the prevention of learning disorders or disorders related to ageing, as well as for coping with increased energy requirements, and which may take the form of a dietary supplement or an actual medicine in its own right, containing the following as its characterising active ingredients: (a) propionyl L-carnitine or one of its pharmacologically acceptable salts; and (b) coenzyme $Q_{10}$.

13 Claims, No Drawings

COMPOSITION FOR PREVENTION AND/OR TREATMENT OF VASCULAR DISEASES, COMPRISING PROPIONYL L-CARNITINE AND COENZYME $Q_{10}$

This application is the US national phase of international application PCT/IT01/00081 filed Feb. 20, 2001 which designated the U.S.

The present invention relates to a combination composition suitable for the prevention and/or treatment of vasculopathic, cardiac, central and peripheral cerebral disturbances and of learning disorders or disorders related to ageing, and which comprises as its characterising ingredients propionyl L-carnitine or one of its pharmacologically acceptable salts and coenzyme $Q_{10}$.

Correspondingly, the composition may take the form and perform the activities of a dietary supplement or of an actual medicine in its own right, depending on whether the action of the composition is meant to be supportive or preventive, or more strictly therapeutic according to the particular individuals for whom it is to be used.

U.S. Pat. No. 4,599,232 discloses a pharmaceutical composition containing L-carnitine or acetyl L-carnitine and coenzyme $Q_{10}$ suitable for the therapeutic treatment of atherosclerotic disorders, myocardial and coronary insufficiency and pathological conditions deriving from tissue anoxia. The composition according to the present invention is more effective than that disclosed in the aforementioned patent, as will be described in detail here below, on account of the potent, synergistic effect exerted by its components.

The action of the "carnitines" in general, and of propionyl L-carnitine in particular, on lipid metabolism is well known, as is their anti-atherosclerotic action and their action against lipid metabolism disorders Propionyl L-carnitine, however, differs from the other "carnitines" in its specific cardiovascular activity, though, like the other "carnitines", it plays an important metabolic role contributing to the β-oxidation of fatty acids and ATP synthesis, particularly at the mitochondrial level.

Propionyl L-carnitine takes part in all the metabolic activities peculiar to the "carnitines", but, unlike the others, it presents more pronounced activity at the vascular level, and particularly in the peripheral circulation, so much so indeed that its use is advocated as a therapeutic agent for the prevention and treatment of various peripheral vascular diseases.

Propionyl L-carnitine is superior to the other carnitines and is also active in conditions in which the other carnitines are unable to exert any activity, and this particular feature is related to a more direct metabolic intervention in processes of energy utilisation at the mitochondrial level and to the presence of the propionyl group which produces a different pharmacological effect compared to other similar molecules and which makes it a distinct chemical entity with properties which are different from and superior to those of the other carnitines.

The particular biochemical and pharmacological effect of propionyl L-carnitine is demonstrated by the numerous studies carried out on this molecule.

Propionyl L-carnitine is a natural component of the pool of carnitines and is synthesised by means of carnitine acetyltransferase starting from propionyl-Coenzyme A.

Its administration in human subjects leads to an increase in plasma concentrations of propionyl L-carnitine which in turn causes an increase in the plasma concentrations of L-carnitine which condition its content in the cells with an increase in their oxidative effect on fatty acids and glucose utilisation. Moreover, muscle carnitine transferase possesses a greater affinity for propionyl L-carnitine than for L-carnitine, and consequently propionyl L-carnitine possesses a greater degree of specificity for cardiac and skeletal muscle. Transporting the propionyl group, propionyl L-carnitine increases the uptake of this component by the muscle cells, particularly the myocardial ones. This may be of particular importance, since propionate can be used by the mitochondria as an anaplerotic substrate and can supply energy in anaerobic conditions.

It should be recalled that propionate cannot be used alone because of its toxic effects.

Apart from these metabolic effects, it should also be recalled that, because of its long alkanoyl chain, propionyl L-carnitine exerts a specific pharmacological action via peripheral vasodilatation and myocardial inotropism in conditions in which the other carnitines are inactive.

Coenzyme $Q_{10}$ is also known for its metabolic activity and for its important role in the transport and utilisation of mitochondrial oxygen necessary for energy transformation for the production of ATP. Beneficial activity in the treatment of various different forms of vascular disease has also been demonstrated for coenzyme $Q_{10}$.

It has now been found that the combination of propionyl L-carnitine and coenzyme $Q_{10}$ powerfully favours cardiovascular and cerebral metabolic activity, enhances learning processes and prevents disorders related to ageing as a result of an unexpected synergistic effect exerted by its components. This synergistic effect is much more evident and more intense than the known effect exerted by the combination of L-carnitine or acetyl L-carnitine and coenzyme $Q_{10}$, and is also manifested in conditions in which L-carnitine and acetyl L-carnitine prove ineffective. The synergistic effect is also evident when propionyl L-carnitine is part of a combination of "carnitines" containing L-carnitine, acetyl L-carnitine, butyryl L-carnitine, valeryl L-carnitine and isovaleryl L-carnitine or their pharmacological acceptable salts or mixtures thereof.

The subject matter of the present invention is therefore a combination composition containing as its characterising active ingredients.

(a) propionyl L-carnitine or one of its pharmacologically acceptable salts; and (b) coenzyme $Q_{10}$, which is particularly useful, thanks to the unexpected, potent, synergistic effects of its components, in the prevention and/or treatment of vasculopathic, cardiac, central and peripheral cerebral disturbances, and for the prevention of learning disorders or disorders related to ageing as well as for coping with increased energy needs.

It has also been found that, advantageously, component (a) may further contains a "carnitine" selected from the group consisting of L-carnitine, acetyl L-carnitine, valeryl L-carnitine, isovaleryl L-carnitine and butyryl L-carnitine or their pharmacologically acceptable salts or mixtures thereof.

In the composition according to the invention, the weight-to-weight ratio of (a) to (b) may range from 1:0.05 to 1:0.5, and preferably from 1:0.05 to 1:0.1.

The composition according to the invention may further contain vitamins, coenzymes, mineral substances, amino acids and/or antioxidants.

The composition can be administered orally in the form of a dietary supplement, or can be administered parenterally, via the rectal, sublingual or transdermal routes in the form of a medication for the treatment of frank pathological states. It can therefore be packaged in solid, semisolid or liquid form, in the form, for example, of tablets, pills, capsules, granules, syrups, ampoules or drops.

The surprising synergistic effect which is produced by the combination of propionyl L-carnitine and coenzyme $Q_{10}$ has been demonstrated in various pharmacological tests (some of which are described here below) selected in such a way as to be strongly predictive for the practical use of this composition in both the preventive/nutritional field and in the strictly therapeutic field.

Toxicology Tests

It is well known that both L-carnitine and coenzyme $Q_{10}$ are well tolerated and do not produce any particular toxic effects even when administered at high doses. Their use in combination also produces no damaging toxicological effects. Tests performed in a group of Sprague-Dawley male rats with a mean body weight of 250 g, to which high doses of proprionyl L-carnitine (2 g/kg) or coenzyme $Q_{10}$ (0.2 g/kg) or the same amounts of the two compounds in combination were given orally in a single administration, failed to reveal any toxic effects or signs of intolerance. Equally well tolerated appeared to be the prolonged administration of a dose of the two compounds in combination given with the diet in rats (propionyl L-carnitine 500 mg/kg/day and coenzyme $Q_{10}$ 50 mg/kg/day).

Even after thirty days of such treatment no cases of mortality were registered in the animals thus treated, nor any reduction of their growth in terms of weight. Blood-chemistry tests performed at the end of treatment revealed no abnormalities in terms of haematic crasis, serum glucose levels and BUN as compared to control animals.

Macro- and microscopic examinations performed on the main organs taken from the sacrificed animals at the end of treatment also appeared normal and the results were comparable to those detected in the control group.

Experimental Thrombotic Vascular Disease Tests

In these tests, the vascular antithrombotic activity of proprionyl L-carnitine and of a combination composition containing propionyl L-carnitine and coenzyme $Q_{10}$, was assessed for the purposes of estimating the protective effect of the composition which is the subject matter of the invention described herein. The method used in these tests was that described by Bekemeier (Bekemeier H., *Agents and Actions*, 16:446, 1985) modified by Bertelli (Bertelli A., *Drugs Exptl. Clin. Res.*, 19:7, 1993) which consists in injecting K-carrageenin (0.5 mg/kg carrageenin, Sigma Chemical St. Louis Mo., USA) into the dorsal artery of the rat tail and, immediately prior to the K-carrageenin injection, 500 pmol/kg of endothelin-1 (Peninsula Laboratories, Belmont Calif., USA) by intravenous injection. With this method, as early as the second hour after injection of K-carrageenin, vascular thrombosis developed which could be estimated by measuring the length of the infarcted portion of the tail, the length of the entire tail and the ratio between the two (% infarcted tail).

The phenomenon was assessed two and twenty-four hours after injection of K-carrageenin. While one group of animals served as controls and received only the thrombosis-inducing substances, another batch of animals (male Sprague-Dawley rats with a mean body weight of 200 g) was divided into different groups which were treated either with a single dose or for four days consecutively prior to the K-carrageenin injection with intravenous or oral doses of the following: i.e. with propionyl L-carnitine (50 mg/kg), or with a combination composition containing propionyl L-carnitine (10 mg/kg), acetyl L-carnitine (10 mg/kg), butyryl L-carnitine (10 mg/kg), isovaleryl L-carnitine (10 mg/kg), L-carnitine (10 mg/kg); or with L-carnitine (50 mg/kg) or acetyl L-carnitine (50 mg/kg); or with coenzyme $Q_{10}$ alone (20 mg/kg) or with coenzyme $Q_{10}$ (20 mg/kg) in combination with the various preparations, or, in the case of oral administrations for the four days prior to the test, with 300 mg/kg of propionyl L-carnitine or L-carnitine or acetyl L-carnitine or a combination of propionyl L-carnitine (75 mg/kg), acetyl L-carnitine (75 mg/kg), L-carnitine (75 mg/kg), butyryl L-carnitine (75 mg/kg), isovaleryl L-carnitine (75 mg/kg) or with 100 mg/kg of coenzyme $Q_{10}$ alone or in combination with the other preparations. Tables 1 and 2 give the results obtained in these tests. It would appear evident that only propionyl L-carnitine or the combination of propionyl L-carnitine and the other carnitines has a protective effect against the onset or severity of the vasculopathy lesions induced, whereas L-carnitine or acetyl L-carnitine administered alone appear to be ineffective.

Coenzyme $Q_{10}$, administered alone, also appears to be poorly effective, whereas its use in combination with propionyl L-carnitine or the carnitine complex enhanced its protective activity, revealing an unexpected, potent, synergistic effect. The enhancement of the effects emerging with the combination of propionyl L-carnitine plus coenzyme $Q_{10}$ is evident both after a single intravenous administration of the two compounds, and even more so after their prolonged administration for four consecutive days, whereas there would not appear to be any significant enhancement with either the coenzyme $Q_{10}$+L-carnitine or the coenzyme $Q_{10}$+acetyl L-carnitine combination.

TABLE 1

Results of experimental thrombosis tests after intravenous administration of products

| Treatment | % inhibition of thrombosis | |
| --- | --- | --- |
| | after 2 h | after 24 h |
| Propionyl L-carnitine | 16.25 ± 0.7 | 26.45 ± 1.9 |
| Carnitine combination | 14.10 ± 0.9 | 19.25 ± 1.1 |
| L-carnitine | 9.5 ± 0.4 | 11.5 ± 0.9 |
| Acetyl L-carnitine | 8.8 ± 0.7 | 10.6 ± 0.8 |
| Coenzyme $Q_{10}$ | 11.7 ± 0.9 | 14.5 ± 1.3 |
| Propionyl L-carnitine + coenzyme $Q_{10}$ | 34.2 ± 2.2 | 49.5 ± 3.9 |
| Carnitine combination + coenzyme $Q_{10}$ | 29.5 ± 1.9 | 39.7 ± 2.6 |
| L-carnitine + coenzyme $Q_{10}$ | 15.6 ± 1.6 | 18.8 ± 1.8 |
| Acetyl L-carnitine + coenzyme $Q_{10}$ | 16.4 ± 1.7 | 20.4 ± 2.1 |

TABLE 2

Results of experimental thrombosis tests after oral administration of products

| Treatment | % inhibition of thrombosis | |
| --- | --- | --- |
| | after 2 h | after 24 h |
| Propionyl L-carnitine | 14.5 ± 0.7 | 30.5 ± 3.3 |
| Carnitine combination | 12.8 ± 0.9 | 20.6 ± 2.4 |
| L-carnitine | 8.5 ± 0.5 | 9.2 ± 1.2 |
| Acetyl L-carnitine | 9.2 ± 0.8 | 11.5 ± 1.5 |
| Coenzyme $Q_{10}$ | 13.8 ± 1.7 | 12.5 ± 1.7 |
| Propionyl L-carnitine + coenzyme $Q_{10}$ | 30.9 ± 2.8 | 56.5 ± 4.0 |
| Carnitine combination + coenzyme $Q_{10}$ | 28.4 ± 1.9 | 35.6 ± 3.1 |
| L-carnitine + coenzyme $Q_{10}$ | 14.6 ± 0.9 | 15.5 ± 1.4 |
| Acetyl L-carnitine + coenzyme $Q_{10}$ | 12.8 ± 1.1 | 18.2 ± 1.6 |

Experimental Cerebral Ischaemia Tests

With another test, the synergistic vascular protective effect exerted by the combination of propionyl L-carnitine and coenzyme $Q_{10}$ was observed.

With this test, the ischaemic area caused by occlusion of middle cerebral artery (MCA) was evaluated using the method described by Scharkey (Scharkey Y., Nature, 371:336, 1994), performed by injecting endothelin-1 (120 pmol in 3 ml) in 5 minutes into anaesthetised rats with a microcannula placed stereotactically in the piriform cortex at the level of the middle cerebral artery. With this method, occlusion of the middle cerebral artery is induced and the resulting ischaemic area can be visualised three days later with transcardiac perfusion of a paraformaldehyde solution (4% in PBS). After extracting the cerebral mass, the latter was placed for twenty-four hours in a fixative containing 10% sucrose, and cryostat sections (20 mm) fixed with resyl violet were examined under the optical microscope. The volume of the infarcted area was calculated according to the method described by Park (Park C. K., Ann. Neurol., 20:150, 1989). Propionyl L-carnitine (100 mg/kg), L-carnitine (100 mg/kg), acetyl L-carnitine (100 mg/kg), or the combination of propionyl L-carnite, L-carnitine, acetyl L-carnitine, butyryl L-carnitine and isovaleryl L-carnitine (100 mg/kg in 1:1 weight-to-weight ratios), coenzyme $Q_{10}$ (50 mg/kg) or coenzyme $Q_{10}$ in combination with the previous compositions were administered to the animals intravenously five minutes after the endothelin injection.

The results of these tests (Table 3) indicate that propionyl L-carnitine possesses good ability to reduce the extent of the ischaemia induced by occlusion of the MCA as a result of injection of endothelin, as do the carnitine complex and coenzyme $Q_{10}$, though to a lesser degree, whereas L-carnitine and acetyl L-carnitine alone have no significant protective effect.

The greatest percentage reduction as compared to controls is that obtainable with the combination of propionyl L-carnitine plus coenzyme $Q_{10}$ or, though to a lesser extent, with the carnitine complex plus coenzyme $Q_{10}$, whereas the protective action of L-carnitine, even when combined with coenzyme $Q_{10}$, would appear to be much less pronounced.

The results of these tests therefore also show the surprising, potent, synergistic effect exerted by the combination of propionyl L-carnitine and coenzyme $Q_{10}$.

TABLE 3

Extent of cerebral ischaemia (volume in mm³) due to occlusion of the MCA (% reduction in volume compared to controls)

|  | Volume |
| --- | --- |
| Propionyl L-carnitine | 30.3 ± 3.6 |
| Coenzyme $Q_{10}$ | 22.2 ± 2.9 |
| L-carnitine | 10.5 ± 0.77 |
| Acetyl L-carnitine | 15.8 ± 1.4 |
| Carnitine combination | 20.8 ± 3.9 |
| Propionyl L-carnitine + coenzyme $Q_{10}$ | 86.8 ± 9.2 |
| L-carnitine + coenzyme $Q_{10}$ | 29.5 ± 8.7 |
| Acetyl L-carnitine + coenzyme $Q_{10}$ | 31.4 ± 4.9 |
| Carnitine combination + coenzyme $Q_{10}$ | 77.5 ± 7.2 |

Myocardial Anti-anoxic Activity Test

This test was used to assess the ability of propionyl L-carnitine to protect the myocardium against the loss of ATP induced by anoxia and to preserve energy capacity even in these conditions.

As is known, the papillary muscle of the rabbit heart perfused and subjected to hypoxia shows a reduction in its ATP energy reserves. An attempt was therefore made to establish whether prior treatment with propionyl L-carnitine, L-carnitine, carnitine combination or coenzyme $Q_{10}$ alone or in combination with propionyl L-carnitine or with the other preparations was capable of preserving normal ATP concentrations in the hypoxic myocardium.

For this test a batch of New Zealand rabbits was used, divided into various groups which received daily intravenous injections for three days consecutively of propionyl L-carnitine (100 mg/kg) or L-carnitine (100 mg/kg) or acetyl L-carnitine (100 mg/kg) or a combination of propionyl L-carnitine (25 mg/kg), acetyl L-carnitine (25 mg/kg), L-carnitine (25 mg/kg), butyryl L-carnitine (25 mg/kg) and isovaleryl L-carnitine (25 mg/kg), or coenzyme $Q_{10}$ (50 mg/kg) alone or coenzyme $Q_{10}$ (50 mg/kg) in combination with the other above-mentioned preparations.

After three days of treatment, all the animals were sacrificed. Sections of papillary muscle measuring 1 mm in diameter and 4–5 mm in thickness were isolated. These samples of papillary muscle were perfused in a thermostatic bath with a saturated solution of 100% $O_2$. The hypoxia was then produced by introducing 100% $N_2$ in the bath in place of $O_2$. The ATP concentrations in papillary muscle were measured using the method described by Strehler (Strehler B. L., Methods in Enzymology, 111, N.Y. Acad. Press, 879, 1957). The analysis was done on tissue samples maintained under oxygen perfusion for 90 min and after a 90 min anoxia period.

The results of this test (Table 4) indicate that both propionyl L-carnitine and coenzyme $Q_{10}$ are capable of at least partially maintaining the ATP concentrations present in papillary muscle, and that preservation of ATP levels is almost complete when the two compounds are given in combination. Much more limited is the protective action of L-carnitine, even when combined with coenzyme $Q_{10}$.

As in the previously described tests, the results of these tests, too, revealed an unexpected and surprising synergistic effect of the combination of propionyl L-carnitine and coenzyme. $Q_{10}$.

Also significant was the synergistic effect observed when coenzyme $Q_{10}$ was combined with the carnitine combination.

TABLE 4

Tests regarding protection of ATP concentrations in the papillary muscle of rabbit heart subjected to hypoxia

|  | ATP concentrations (mol/g tissue) | |
| --- | --- | --- |
| Treatment | Before hypoxia | After hypoxia |
| Controls | 1.61 ± 0.71 | 0.44 ± 0.062 |
| Propionyl L-carnitine | 1.58 ± 0.64 | 0.64 ± 0.055 |
| Carnitine combination | 1.60 ± 0.45 | 0.59 ± 0.065 |
| L-carnitine | 1.55 ± 0.80 | 0.50 ± 0.045 |
| Acetyl L-carnitine | 1.58 ± 0.98 | 0.54 ± 0.075 |
| Coenzyme $Q_{10}$ | 1.65 ± 0.70 | 0.64 ± 0.068 |
| Propionyl L-carnitine + coenzyme $Q_{10}$ | 1.59 ± 0.85 | 1.58 ± 0.82 |
| Carnitine combination + coenzyme $Q_{10}$ | 1.60 ± 0.72 | 1.05 ± 0.39 |
| L-carnitine + coenzyme $Q_{10}$ | 1.55 ± 0.65 | 0.64 ± 0.056 |
| Acetyl L-carnitine + coenzyme $Q_{10}$ | 1.64 ± 0.90 | 0.70 ± 0.048 |

Learning Tests

These tests were performed in mice using the water maze procedure as described by Morris (Morris R., J. Neurosci. Meth., 11:47, 1984) and modified by Lin (Lin Y., Acta Pharmacol. Sin., 19:413, 1998). The procedure consists in placing, in a maze situated in a tank containing water (80 cm×50 cm×20 cm) 10 cm deep, mice of both sexes weighing approximately 20 g each, which, after a suitable period of training in the task of finding their way back to the final platform and after selecting those that took less than 20 min to do so, were divided into various groups. The animals were administered either a single intraperitoneal dose or oral doses for three consecutive days of propionyl L-carnitine, carnitine combination, L-carnitine, acetyl L-carnitine, or coenzyme $Q_{10}$ alone, or coenzyme $Q_{10}$ in combination with the various above-mentioned preparations.

The doses administered intraperitoneally were 100 mg/kg of propionyl L-carnitine, 100 mg/kg of L-carnitine, 100 mg/kg of acetyl L-carnitine, 100 mg/kg of carnitine combination (in 1:1 weight-to-weight ratios between the individual components: propionyl L-carnitine 20 mg/kg, acetyl L-carnitine 20 mg/kg, L-carnitine 20 mg/kg, butyryl L-carnitine 20 mg/kg, isovaleryl L-carnitine 20 mg/kg) and 50 mg/kg of coenzyme $Q_{10}$.

The doses administered orally for three consecutive days were 300 mg/kg of propionyl L-carnitine, 300 mg/kg of carnitine combination (propionyl L-carnitine 60 mg/kg, L-carnitine 60 mg/kg, acetyl L-carnitine 60 mg/kg, butyryl L-carnitine 60 mg/kg, isovaleryl L-carnitine 60 mg/kg), 300 mg/kg of L-carnitine, 300 mg/kg of acetyl L-carnitine, or 20 mg/kg of coenzyme $Q_{10}$ alone or in combination with the above-mentioned preparations.

Both intraperitoneal and oral administration were carried out one hour prior to the start of the test. Half an hour before the start all the animals were administered scopolamine intraperitoneally at the dose of 3 mg/kg. As is known, scopolamine induces abnormalities of spatial orientation and prolongs latency time in finding the way to reach the platform.

After the test the latency time to reach the platform was calculated for each animal.

As can be seen from the results in Table 5, these tests also showed an unexpected marked degree of synergy between propionyl L-carnitine and coenzyme $Q_{10}$. The surprising synergistic action is more evident in the group of animals subjected to prolonged treatment than in those receiving a single dose of the combination tested.

The carnitine combination also showed significant activity in this test, while L-carnitine proved inactive and acetyl L-carnitine exerted only poor activity, whether administered alone or in combination with coenzyme $Q_{10}$.

TABLE 5

| | Learning test | |
|---|---|---|
| Treatment | Administration (I.P.) Latency period (seconds) | Administration (per os, 3 days) Latency period (seconds) |
| Propionyl L-carnitine | 32 ± 12 | 30 ± 16 |
| Carnitine combination | 35 ± 20 | 33 ± 18 |
| Acetyl L-carnitine | 38 ± 18 | 36 ± 10 |
| L-carnitine | 40 ± 20 | 39 ± 21 |
| Coenzyme $Q_{10}$ | 31 ± 18 | 31 ± 12 |
| Propionyl L-carnitine + coenzyme $Q_{10}$ | 19 ± 10 | 14 ± 9 |
| Carnitine combination + coenzyme $Q_{10}$ | 20 ± 12 | 16 ± 11 |
| L-carnitine + coenzyme $Q_{10}$ | 29 ± 16 | 28 ± 9 |
| Acetyl L-carnitine + coenzyme $Q_{10}$ | 38 ± 21 | 34 ± 16 |

Provided here below by way of illustration are a number of examples of compositions according to the invention described herein, though the possible compositions are by no means limited to these.

| | |
|---|---|
| 1) Propionyl L-carnitine | 500 mg |
| Coenzyme $Q_{10}$ | 50 mg |
| 2) Propionyl L-carnitine | 1 g |
| Coenzyme $Q_{10}$ | 100 mg |
| 3) Propionyl L-carnitine | 250 mg |
| Coenzyme $Q_{10}$ | 25 mg |
| 4) Carnitine combination | 500 mg |
| (propionyl L-carnitine 125 mg, acetyl L-carnitine 125 mg, isovaleryl L-carnitine 125 mg, L-carnitine 125 mg) | |
| Coenzyme $Q_{10}$ | 50 mg |
| 5) Propionyl L-carnitine | 500 mg |
| Coenzyme $Q_{10}$ | 25 mg |
| Vit. E | 5 mg |
| Vit. $B_1$ | 1 mg |
| Vit. $B_2$ | 2 mg |
| Vit. $B_6$ | 1 mg |
| Vit. D | 500 I.U. |
| Folic acid | 100 μg |
| Vit. PP | 20 mg |
| Vit $B_{12}$ | 100 μg |
| Magnesium stearate | 5 mg |
| Zinc glycinate | 10 mg |
| Selenomethionine | 50 μg |
| 6) Carnitine combination | 500 mg |
| (propionyl L-carnitine 125 mg, acetyl L-carnitine 125 mg, isovaleryl L-carnitine 125 mg, L-carnitine 125 mg) | |
| Coenzyme $Q_{10}$ | 25 mg |
| Vit. E | 5 mg |
| Vit. $B_1$ | 1 mg |
| Vit. $B_2$ | 2 mg |
| Vit. $B_6$ | 1 mg |
| Vit. D | 500 I.U. |
| Folic acid | 100 μg |
| Vit. PP | 20 mg |
| Vit. $B_{12}$ | 100 μg |
| Magnesium stearate | 5 mg |
| Zinc glycinate | 10 mg |
| Selenomethionine | 50 μg |

What is meant by a pharmacologically acceptable salt of L-carnitine or of an alkanoyl L-carnitine is any salt of these with an acid which does not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

A list of FDA-approved pharmacologically acceptable acids is given in *Int. J. Pharm.*, 33, 1986, 201–217, the latter publication being incorporated in the present specification by reference.

What is claimed is:

1. A combination composition which consists essentially of:
   (a) propionyl L-carnitine or a pharmacologically acceptable salt thereof; and
   (b) coenzyme $Q_{10}$.

2. A combination which consists essentially of:
   (a) propionyl L-carnitine or a pharmaceutically acceptable salt thereof:
   (b) coenzyme $Q_{10}$; and
   (c) at least one "-carnitine-" selected from the group consisting of L-carnitine, acetyl L-carnitine, valery L-carnitine, isovalery L-carnitine and butyryl L-carnitine or their pharmacologically acceptable salts or mixtures thereof.

3. The composition of claim 1 or 2, wherein the weight ratio (a):(b) ranges from 1:0.05 to 1:0.1.

4. The composition of claim 1 or 2, wherein the weight ratio (a):(b) ranges from 1:0.05 to 1:0.1.

5. The composition of claim 1 or 2, wherein the pharmacologically acceptable salt is selected from the group consisting of chloride; bromide; iodide, aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate; acid oxalate; sulphate, acid sulphate; trichloroacetate; trifluoroacetate and methane syulphonate.

6. The composition of claim 1 or claim 2, orally administrable, in the form of a dietary supplement.

7. The composition of claim 1 or claim 2, orally, parenterally, rectally, sublingually or transdermally administrable, in the form of a medicament.

8. The dietary supplement of claim 6, in solid, semi-solid or liquid form.

9. The composition of claim 7, manufactured in solid, semi-solid or liquid form.

10. The dietary supplement of claim 8, in the form of tablets, lozenges, pills, capsules, granulates, syrups, vials or drops.

11. The composition of claim 9, in the form of tablets, lozenges, pills, capsules, graulates, syrups, vials or drops.

12. A method for the treatment of vasculopathic, cardiac, central and peripheral cerebral disturbances and of learning disorders or disorders related to ageing comprises administering to a subject in need thereof a combination composition consisting essentially of the following components:

(a) propionyl L-carnitine or a pharmacologically acceptable salt thereof, and (b) coenzyme $Q_{10}$.

13. A method for the treatment of vasculopathic, cardiac, central and peripheral cerebral disturbances and of learning disorders or disorders related to ageing which comprises administering to a subject in need thereof a combination composition consisting essentially of the following components:

(a) propionyl L-carnitine or a pharmacologically acceptable salt thereof, (b) coenzyme $Q_{10}$, and (c) at least one carnitine selected from the group consisting of L-carnitine, acetyl L-carnitine, valeryl L-carnitine, isovaleryl L-carnitine and butyryl L-carnitine or their pharmacologically acceptable salts or mixtures thereof.

* * * * *